United States Patent
Baumann et al.

(10) Patent No.: US 8,242,123 B2
(45) Date of Patent: Aug. 14, 2012

(54) INSECTICIDAL METHODS USING 4-AMINO-5-CHLORO-THIENO[2,3-D]-PYRIMIDINE COMPOUNDS

(75) Inventors: Ernst Baumann, Dudenhofen (DE); Henricus Maria Martinus Bastiaans, Usingen (DE); Wolfgang von Deyn, Neustadt (DE); Michael Puhl, Lampertheim (DE); Michael Rack, Eppelheim (DE); Douglas D. Anspaugh, Apex, NC (US); Deborah L. Culbertson, Fuquay Varina, NC (US); Hassan Oloumi-Sadeghi, Raleigh, NC (US)

(73) Assignee: Merial Limited, Duluth, GA (US)

( * ) Notice: Subject to any disclaimer, the term of this patent is extended or adjusted under 35 U.S.C. 154(b) by 757 days.

(21) Appl. No.: 12/301,511

(22) PCT Filed: May 15, 2007

(86) PCT No.: PCT/EP2007/054717
§ 371 (c)(1),
(2), (4) Date: Nov. 19, 2008

(87) PCT Pub. No.: WO2007/135029
PCT Pub. Date: Nov. 29, 2007

(65) Prior Publication Data
US 2009/0203524 A1    Aug. 13, 2009

Related U.S. Application Data

(60) Provisional application No. 60/802,354, filed on May 22, 2006.

(51) Int. Cl.
*C07D 495/04* (2006.01)
*A61K 31/519* (2006.01)
*A01N 43/90* (2006.01)
*A61P 33/00* (2006.01)

(52) U.S. Cl. ............... 514/260.1; 544/278; 504/241; 504/100

(58) Field of Classification Search ............ 544/278; 514/260.1
See application file for complete search history.

(56) References Cited

U.S. PATENT DOCUMENTS

| 4,146,716 A | 3/1979 | Cox et al. |
| 4,196,207 A | 4/1980 | Webber |
| 5,571,815 A | 11/1996 | Schaper et al. |

FOREIGN PATENT DOCUMENTS

| CA | 2038521 | 9/1991 |
| DE | 26 54 090 | 6/1977 |
| EP | 0 370 704 | 5/1990 |
| EP | 0 447 891 | 9/1991 |
| EP | 447891 | * 9/1991 |
| EP | 0 045 2002 | 10/1991 |
| JP | 2004 238380 | 8/2004 |
| WO | WO 93/19050 | 9/1993 |
| WO | WO 2006/047397 | 5/2006 |

OTHER PUBLICATIONS

International Search Report for International Application No. PCT/EP2007/054717; International Filing Date: May 15, 2007; Date of Completion: Sep. 18, 2007; Date of Mailing: Sep. 28, 2007.
International Preliminary Report on Patentability for International Application No. PCT/EP2007/054717; International Filing Date: May 15, 2007; Date of Issuance: Nov. 27, 2008.

* cited by examiner

*Primary Examiner* — Susanna Moore
(74) *Attorney, Agent, or Firm* — Judy Jarecki-Black; John Ezcurva; Merial Limited

(57) ABSTRACT

The present invention relates to new insecticidal methods of using 4-Amino-5-chloro-thieno[2,3-d]-pyrimidine compounds of formula (I) wherein $R^1$, $R^2$, $R^3$ and A are defined as in the description. The present invention relates to insecticidal methods of applying such compounds of formula (I), and to new derivatives of compounds of formula (I).

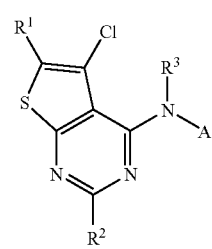

(I)

18 Claims, No Drawings

INSECTICIDAL METHODS USING 4-AMINO-5-CHLORO-THIENO[2,3-D]-PYRIMIDINE COMPOUNDS

This application is a National Stage application of International Application No. PCT/EP2007/054717 filed May 15, 2007, which claims the benefit of U.S. Provisional Application No. 60/802,354, filed May 22, 2006, the entire contents of which is hereby incorporated herein by reference.

The present invention relates to new insecticidal methods of using 4-Amino-5-chloro-thieno[2,3-d]-pyrimidine compounds and salts thereof.

Animal pests destroy growing and harvested crops and attack wooden dwelling and commercial structures, causing large economic loss to the food supply and to property.

While a large number of pesticidal agents are known, due to the ability of target pests to develop resistance to said agents, there is an ongoing need for new agents for combating animal pests. In particular, animal pests such as insects and acaridae are difficult to be effectively controlled.

It is therefore an object of the present invention to provide methods and compounds having a good pesticidal activity, especially against difficult to control insects and acaridae.

It has been found that these objects are solved by 4-Amino-5-chloro-thieno[2,3-d]-pyrimidine derivatives of the general formula I:

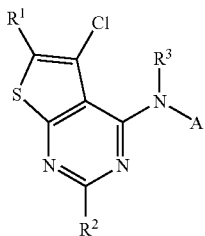

formula I wherein
$R^1$ is selected from hydrogen, halogen, formyl, $C_1$-$C_{10}$-alkyl, $C_1$-$C_{10}$-alkenyl, $C_1$-$C_{10}$-alkynyl, $C_1$-$C_{10}$-haloalkyl, $C_1$-$C_{10}$-haloalkenyl, $C_1$-$C_{10}$-haloalkynyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino, di($C_1$-$C_{10}$-alkyl)amino, CN, CNOH, CNOCH$_3$ or CNOC$_2$H$_5$;
$R^2$ is selected from hydrogen, halogen, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino or di($C_1$-$C_{10}$-alkyl)amino;
$R^3$ is hydrogen or $C_1$-$C_{10}$-alkyl;
A is

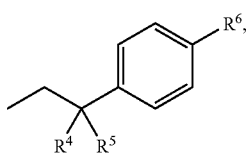

(A1)

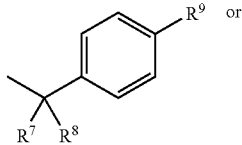

(A2)

or

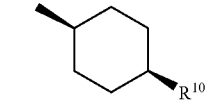

(A3)

wherein
$R^4$, $R^5$, $R^7$ are selected independently from one another from hydrogen or $C_1$-$C_{10}$-alkyl;
$R^8$ $C_1$-$C_{10}$-alkyl;
$R^6$, $R^9$ is selected from halogen, $C_1$-$C_{10}$-alkyl, $C_1$-$C_{10}$-haloalkyl, $C_1$-$C_{10}$-alkoxy, $C_1$-$C_{10}$-haloalkoxy;
$R^{10}$ is $C_1$-$C_{10}$-alkyl or $C_1$-$C_{10}$-haloalkyl;
and/or at least one agriculturally or veterinary acceptable salt thereof.

Depending on the substitution pattern, the compounds of formula I can contain one or more chiral centers, in which case they are present as enantiomer or diastereomer mixtures. Subject matter of this invention are not only compositions containing these mixtures but also those containing the pure enantiomers or diastereomers.

The present invention relates therefore to following insecticidal methods applying such compounds of formula I.

It was an object of the present invention to provide methods of combating and controlling animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one 4-Amino-5-chloro-thieno[2,3-d]-pyrimidine compound of formula I and/or at least one agriculturally acceptable salt thereof;

It was further an object of the present invention to provide methods for protecting crops from attack or infestation by animal pests, which comprises contacting a crop or a growing plant with a pesticidally effective amount of at least one 4-Amino-5-chloro-thieno[2,3-d]-pyrimidine compound of formula I and/or at least one agriculturally acceptable salt thereof;

Another object of the present invention was to provide methods for protecting seeds from soil insects and seedlings' roots and shoots from soil and foliar insects comprising contacting the seeds before sowing and/or after pregermination with at least one 4-Amino-5-chloro-thieno[2,3-d]-pyrimidine compound of formula I and/or at least one agriculturally acceptable salt thereof;

And another object of the present invention was to provide methods for treating, controlling, preventing or protecting animals against infestation or infection by parasites by administering to the animals a parasitically effective amount of at least one 4-Amino-5-chloro-thieno[2,3-d]-pyrimidine compound and/or at least one a veterinary acceptable salt thereof. Object of the invention are also methods of using at least one compound of the formula I and/or a veterinary acceptable salts thereof, for combating parasites in and on animals by treating the parasites with an parasitical active amount thereof;

Further, the present invention relates also to new cyclohexyl substituted 4-Amino-5-chloro-thieno[2,3-d]-pyrimidine compounds of the general formula I-A3, to their agricultural or veterinary useful salts and to veterinary or agricultural compositions comprising them and at least one inert liquid and/or solid agronomically acceptable carrier:

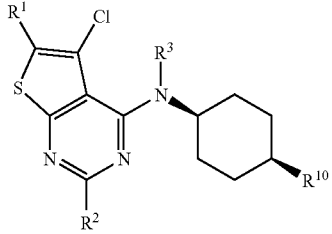

(formula I-A3)

wherein
R$^1$ is selected from hydrogen, halogen, formyl, $C_1$-$C_{10}$-alkyl, $C_1$-$C_{10}$-alkenyl, $C_1$-$C_{10}$-alkynyl, $C_1$-$C_{10}$-haloalkyl, $C_1$-$C_{10}$-haloalkenyl, $C_1$-$C_{10}$-haloalkynyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino, di($C_1$-$C_{10}$-alkyl)amino, CN, CNOH, CNOCH$_3$ or CNOC$_2$H$_5$;
R$^2$ is selected from hydrogen, halogen, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino or di($C_1$-$C_{10}$-alkyl)amino;
R$^3$ is hydrogen or $C_1$-$C_{10}$-alkyl;
R$^{10}$ is $C_1$-$C_{10}$-alkyl or $C_1$-$C_{10}$-haloalkyl;

Thienopyrimidines are known and have been described in prior art. 4-Aminothienopyrimidines have been mentioned in EP-A 0370704 as aralkylamine derivatives having bactericidal properties. 4-Amino-thienopyrimidine derivative compositions have also been described in DE-A 2654090 for controlling fungal, viral and bacterial plant disease and insect damage. In EP-A 0452002 N-substituted-thienopyrimidin-4-amines having fungicidal, insecticidal and miticidal utility are disclosed. JP-A 2004-238380 describes the preparation of 4-phenylethylaminopyrimidine and their uses as pesticides. Thieno-pyrimidine compounds having fungicidal activity have been described in WO 2006/047397. N-substituted 4-Amino-5-chloro-thieno[2,3-d]-pyrimidine compounds with herbicidal, growth-regulating and insecticidal activities have been described in EP-A 0447891.

Compared to those compounds disclosed in EP-A 0447891, the 4-Amino-5-chloro-thieno[2,3-d]-pyrimidine compounds of the present invention show surprisingly a better insectidal activity. Especially such compounds having a para-substituted six-membered cyclic ring attached to the nitrogen of the amino-group.

The compounds of the formula I, and their agriculturally or veterinary acceptable salts are highly active against animal pest, i.e. harmful arthropodes and nematodes, especially against difficult to control insects and acaridae.

Moreover, salts of the compounds of the formula I are preferably agriculturally or veterinary acceptable salts. They can be formed in a customary method, e.g. by reacting the compound with an acid of the anion in question if the compound of formula I has a basic functionality or by reacting an acidic compound of formula I with a suitable base.

Useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium (NH$_4$$^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of formula I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term $C_1$-$C_6$-alkoxy-$C_1$-$C_6$-alkyl as used herein refers to alkyl having 1 to 6 carbon atoms, e.g. like specific examples mentioned above, wherein one or more hydrogen atom(s) of the alkyl radical is/are replaced by a $C_1$-$C_6$-alkoxy group.

With respect to the different methods of use according to the invention, particular preference is given to the following meanings of the substituents and variables of the 4-Amino-5-chloro-thieno[2,3-d]-pyrimidine compounds of formula I, in each case on their own or in combination:

Preferred are 4-Amino-5-chloro-thieno[2,3-d]-pyrimidine compounds of formula I, wherein A is A1.

Preferred are 4-Amino-5-chloro-thieno[2,3-d]-pyrimidine compounds of formula I, wherein A is A2.

Especially preferred are 4-Amino-5-chloro-thieno[2,3-d]-pyrimidine compounds of formula I according to claim 1, wherein A is A2 and represents an S-enantiomer.

Preferred are 4-Amino-5-chloro-thieno[2,3-d]-pyrimidine compounds of formula I, wherein A is A3.

Preferred are 4-Amino-5-chloro-thieno[2,3-d]-pyrimidine compounds of formula I, wherein $R^1$, $R^2$ are selected independently from one another from hydrogen or $C_1$-$C_6$-alkyl.

Preferred are 4-Amino-5-chloro-thieno[2,3-d]-pyrimidine compounds of formula I, wherein $R^5$ or $R^7$ is hydrogen.

Preferred are 4-Amino-5-chloro-thieno[2,3-d]-pyrimidine compounds of formula I, wherein $R^{10}$ is a branched $C_3$-$C_{10}$-alkyl.

Especially preferred are 4-Amino-5-chloro-thieno[2,3-d]-pyrimidine compounds of formula I, wherein $R^{10}$ is iso-propyl, sec-butyl or tert-butyl.

Preparation Methods

4-Amino-5-chloro-thieno[2,3-d]pyrimidine compounds of formula I according to the present invention can be prepared starting from thiophen compounds (II) as described in EP 0447 891 B.

A thiophen derivative of formula (II)

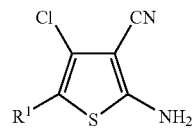

(II)

wherein $R^1$ is defined as above, is reacted with a dialkyl amide (III)

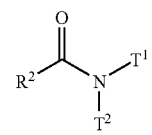

(III)

wherein $T^1$ and $T^2$ are independently from one another $C_1$-$C_4$-alkyl or form together with the nitrogen a 5 to 7-membered saturated heterocyclus and $R^2$ is defined as above, in presence of an excess of a phosphoryl halogenide as e.g. 2 to 20 mol of phosphoryl chloride or phosphoryl bromide compared to 1 mol of (II) in order to provide a thieno(2,3-d)-pyrimidine derivative of formula (Ia)

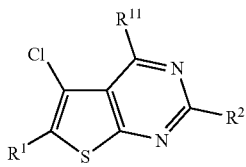
(Ia)

wherein $R^{11}$ is chloro or bromo.

Compounds of formula (Ia) obtained as described above can be converted by substitution of the halogen atom in position 4 by another nucleophilic rest according to known methods as described in 'The Chemistry of Heterocyclic compounds', "The pyrimidines", ed. D. J. Brown, J. Wiley & Sony, New York, London, Vol. 16, (1962); Vol. 16, Suppl. 1, Vol. 16, Suppl. 2 (1985).)

They are converted to the corresponding compounds of formula I by the substitution of $R^{11}$ by $NR^3A$ as described in EP-A 447 891.

Examples of suitable dialkyl-amides (III) are N,N-dimetyhl-formamide, N,N-dimethylacetamide, N,N-diethyl-formamide, N,N-diethyl-acteamide, N,N-dimethyl-propionamide and N,N-dimethyl benzoic acid amide.

As mentioned above, the reaction has to be conducted in presence of an excess of phosphoryl chloride or phosphoryl bromide compared to the thiophen derivative (II). Advantageously the reaction may take place with the phosphoryl halogenide as a solvent. Preferably 2 to 6 mol of phosphoryl halogenide are used per mol of the thiophen derivative (II).

In general the molar ratio of the thiophen derivative (II) to the N,N-dialkyl amide (III) is from 1:1 to 1:5.

The reaction is usually conducted in an inert solvent as chlorobenzole, nitrobenzole, benzoic acid methyl ester, methylene chloride, dichlorobenzol, trichlorobenzole, benzoic acid ethyl ester, chloroform, tetrachlorocarbon, one of the N,N-dialkyl amides listed above, trichloroethane, hexamethylphosphoric triamide (HMPT) or tetrachloroethylene. Preferred solvent are phosphoryl chloride and phosphoryl bromide or one of the N,N-dialkyl amides listed above.

The reaction has a sufficient reaction speed above 20° C. At temperatures above 150° C. the reaction specificy drops. Preferably the reaction is conducted in a temperature range of 50 to 110° C.

By the use of catalytic amounts of a lewis acid as potassium chloride, sodium chloride, iron (III) chloride, aluminium chloride, zinc chloride, tin chloride, antimony pentafluoride, boron trifluoride or titanium tetrachloride or of a basic catalyst as N,N-dimethyl aniline or N,N-diethyl aniline an increase of yield and an enhancement of reaction speed can be achieved.

Another process of preparation of 4-amino-5-chloro-thieno[2,3-d]pyrimidine compounds of formula I is provided by reacting according to common practise compounds of formula (IV)

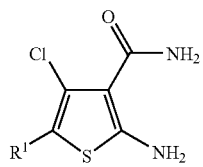
(IV)

wherein $R^1$ is defined as above, with an acid anhydride, that contains at least a rest $R^2$—CO—, or a carbonic acid $R^2$—COOH, or an adduct of a carbonic acid and a lewis acid, wherein $R^2$ has the respective meaning as described above, to compounds of formula (Ib):

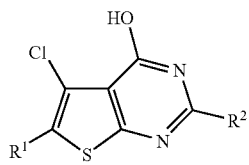
(Ib)

Compounds of formula (Ib) are converted with a phosphoryl halogenid to compounds of formula (Ia) as defined above. It is suitable in certain cases to conduct this conversion in two steps, thereby isolating the intermediate compounds of formula (VI):

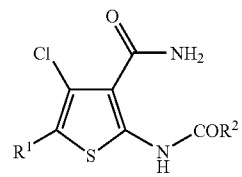
(VI)

In general the acid anhydride or the adduct is used in amounts from 100 to 500 mol-%, preferably from 100 to 300 mol-%, in regard of compounds (VI).

The carbonic acid anhydrides containing at least one rest $R^2$—CO—, can be provided out of two carbonic acids $R^2$—COOH, as pivalic acid, propionic acid or acetic acid; or out of one carbonic acid $R^2$—COOH and one oxo acid, as phosphoric acid or sulfuric acid.

Preferred carbonic acids $R^2$—COOH are those with 1 to 4 carbon atoms, especially formic acid and acetic acid.

Further, adducts of a carbonic acid $R^2$—COOH and a lewis acid, as zinc chloride, boron trifluoride and titanium tetrachloride are also suitable.

The conversion from (IV) to (Ib) is advantageously conducted in an inert solvent, as N,N-dialkyl amides, preferably N,N-dimethyl formamide and N,N-dimethyl acteamide, N-methyl-pyrrolidone, N,N-dimethyl propylene urea or hexamethylphosphoric triamide at temperatures from (−10) to 150° C., preferably from 20 to 120° C., more preferably from 80 to 120° C.

In order to isolate intermediate compounds (VI), the reaction temperature should be chosen from (−10) to 80° C.

In general a base as triethylamine, N-methyl-pyrrolidone or N,N-dimetyhl aniline should be added in an excess of 1 to 10-times, preferably in an excess of 1 to 5-times, compared to the carbonic acid anhydride, the carbonic acid or the carbonic-acid-lewis-acid-adduct.

The addition of a water removing agent as dicyclohexyl carboimid or a vilsmeier reagent can speed up the reaction and increase the yield of compounds of formula (Ib).

The hydroxy group in position 4 of compound of formula (Ib) can be substituted by chloro or bromo according to common practise, e.g. with phosphoryl chloride or phosphoryl bromide.

Finally chloro and bromo in position 4 is substituted by $NR^3A$ as described e.g. in EP-A 447 891.

Furthermore, by conversion of thiophen compounds of formula (II) with orthoesters (V), wherein $R^{12}$ is a $C_1$-$C_4$-alkyl, to derivatives of formula (VI), and subsequent cyclysation in presence of an amine NR³A, thieno[2,3-d]pyrimidine compounds of formula (I) according to the present invention can be obtained.

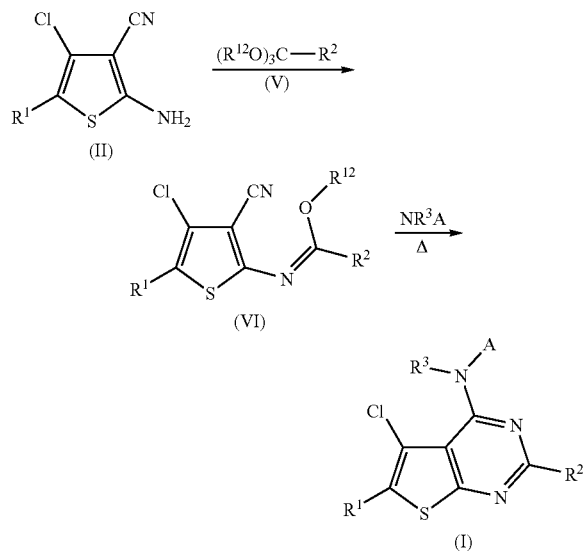

The latest described reaction scheme is known from DE-A 26 54 090. The thiophene derivative (II) and (IV) can be obtained according to the instructions disclosed in EP-A1-0193 885.

In order to obtain salts, which are suitable for agricultural or veterinary use, the 4-amino-5-chloro-thieno[2,3-d]pyrimidine compounds of formula I can be reacted with conventional salt builders as hydrochloric acid, hydrobromic acid, hydroiodic acid, sulfuric acid, phosphoric acid, formic acid, acetic acid, oxalic acid, benzene sulfonic acid, p-toluol-sulfonic acid, dodecylbenzene sulfonic acid, methyl bromide, dimethyl sulfate or diethyl sulfate in temperature range of 0 to 150° C., preferably 20 to 120° C.

The formation of the salt is usually conducted in a dissolving or diluting agent. Suitable are e.g. aliphatic hydrocarbons as n-pentane, n-hexane or petrol ether, aromatic hydrocarbons, as benzole, toluole or xylole, benzine or ethers as diethyl ether, methyltert.-butyl ether, tetrahydrofurane or dioxane, further ketones, as acetone, methyl-ethylketone or methyl-isopropyl-ketone, as well as halogenated hydrocarbons as chlorobenzole, methylene chloride, ethylenen chloride, chloroform or tetrachlor ethylene. Also mixtures of those solvents can be used.

For the preparation of salts of compounds of formula I the educts are employed usually in a stoichiometric ratio. The excess of one or the other component can be useful.

In the preparation methods described, the variables $R^1$, $R^2$, and $R^3$ have the meanings as defined above, in particular the meanings mentioned as being preferred.

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

Applications

The compounds of the formula I, and their salts are in particular suitable for efficiently controlling arthropodal pests such as arachnids, myriapedes and insects as well as nematodes.

In particular, they are suitable for controlling insect pests, such as insects from the order of Lepidoptera: for example *Agrotis ypsilon*, *Agrotis segetum*, *Alabama argillacea*, *Anticarsia gemmatalis*, *Argyresthia conjugella*, *Autographa gamma*, *Bupalus piniarius*, *Cacoecia murinana*, *Capua reticulana*, *Chematobia brumata*, *Choristoneura fumiferana*, *Choristoneura occidentalis*, *Cirphis unipuncta*, *Cydia pomonella*, *Dendrolimus pini*, *Diaphania nitidalis*, *Diatraea grandiosella*, *Earias insulana*, *Elasmopalpus lignosellus*, *Eupoecilia ambiguella*, *Evetria bouliana*, *Feltia subterranea*, *Galleria mellonella*, *Grapholitha funebrana*, *Grapholitha molesta*, *Heliothis armigera*, *Heliothis virescens*, *Heliothis zea*, *Hellula undalis*, *Hibernia defoliaria*, *Hyphantria cunea*, *Hyponomeuta malinellus*, *Keiferia lycopersicella*, *Lambdina fiscellaria*, *Laphygma exigua*, *Leucoptera coffeella*, *Leucoptera scitella*, *Lithocolletis blancardella*, *Lobesia botrana*, *Loxostege sticticalis*, *Lymantria dispar*, *Lymantria monacha*, *Lyonetia clerkella*, *Malacosoma neustria*, *Mamestra brassicae*, *Orgyia pseudotsugata*, *Ostrinia nubilalis*, *Panolis flammea*, *Pectinophora gossypiella*, *Peridroma saucia*, *Phalera bucephala*, *Phthorimaea operculella*, *Phyllocnistis citrella*, *Pieris brassicae*, *Plathypena scabra*, *Plutella xylostella*, *Pseudoplusia includens*, *Rhyacionia frustrana*, *Scrobipalpula absoluta*, *Sitotroga cerealella*, *Sparganothis pilleriana*, *Spodoptera eridania*, *Spodoptera frugiperda*, *Spodoptera littoralis*, *Spodoptera litura*, *Thaumatopoea pityocampa*, *Tortrix viridana*, *Trichoplusia ni* and *Zeiraphera canadensis*, Coleoptera (beetles), for example *Agrilus sinuatus*, *Agriotes lineatus*, *Agriotes obscurus*, *Amphimallus solstitialis*, *Anisandrus dispar*, *Anthonomus grandis*, *Anthonomus pomorum*, *Atomaria linearis*, *Blastophagus piniperda*, *Blitophaga undata*, *Bruchus rufimanus*, *Bruchus pisorum*, *Bruchus lentis*, *Byctiscus betulae*, *Cassida nebulosa*, *Cerotoma trifurcata*, *Ceuthorrhynchus assimilis*, *Ceuthorrhynchus napi*, *Chaetocnema tibialis*, *Conoderus vespertinus*, *Crioceris asparagi*, *Diabrotica longicornis*, *Diabrotica 12-punctata*, *Diabrotica virgifera*, *Epilachna varivestis*, *Epitrix hirtipennis*, *Eutinobothrus brasiliensis*, *Hylobius abietis*, *Hypera brunneipennis*, *Hypera postica*, *Ips typographus*, *Lema bilineata*, *Lema melanopus*, *Leptinotarsa decemlineata*, *Limonius californicus*, *Lissorhoptrus oryzophilus*, *Melanotus communis*, *Meligethes aeneus*, *Melolontha hippocastani*, *Melolontha melolontha*, *Oulema oryzae*, *Ortiorrhynchus sulcatus*, *Otiorrhynchus ovatus*, *Phaedon cochleariae*, *Phyllotreta chrysocephala*, *Phyllophaga* sp., *Phyllopertha horticola*, *Phyllotreta nemorum*, *Phyllotreta striolata*, *Popillia japonica*, *Sitona lineatus* and *Sitophilus granaria*, Diptera, for example *Aedes aegypti*, *Aedes vexans*, *Anastrepha ludens*, *Anopheles maculipennis*, *Ceratitis capitata*, *Chrysomya bezziana*, *Chrysomya hominivorax*, *Chrysomya macellaria*, *Contarinia sorghicola*, *Cordylobia anthropophaga*, *Culex pipiens*, *Dacus cucurbitae*, *Dacus oleae*, *Dasineura brassicae*, *Fannia canicularis*, *Gasterophilus intestinalis*, *Glossina morsitans*, *Haematobia irritans*, *Haplodiplosis equestris*, *Hylemyia platura*, *Hypoderma lineata*, *Liriomyza sativae*, *Liriomyza trifolii*, *Lucilia caprina*, *Lucilia cuprina*, *Lucilia sericata*, *Lycoria pectoralis*, *Mayetiola* destructor, Musca autumnalis, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa, Thysanoptera (thrips), e.g. Dichromothrips spp., Frankliniella fusca, Frankliniella occidentalis, Frankliniella tritici, Scirtothrips citri, Thrips oryzae, Thrips palmi and Thrips tabaci, Hymenoptera e.g. Athalia rosae, Atta cephalotes, Atta sexdens, Atta texana, Hoplocampa minuta, Hoplocampa testudinea, Lasius niger, Monomorium pharaonis, Solenopsis geminata and Solenopsis invicta, Heteroptera, e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis and Thyanta perditor, Homoptera (in particular aphids), e.g. Acyrthosiphon onobrychis, Adelges laricis, Aphidula nasturtii, Aphis craccivora, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisa tabaci, Bemisa argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, and Viteus vitifolii, Isoptera (termites), e.g. Calotermes flavicollis, Leucotermes flavipes, Reticulitermes grassei, Reticulitermes lucifugus, Reticulitermes santonensis und Termes natalensis, Orthoptera, e.g. Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus, and Collembola (springtails), e.g. Onychiurus ssp.

They are also suitable for controlling Nematodes: plant parasitic nematodes such as root knot nematodes, Meloidogyne hapla, Meloidogyne incognita, Meloidogyne javanica, and other Meloidogyne species; cyst-forming nematodes, Globodera rostochiensis and other Globodera species; Heterodera avenae, Heterodera glycines, Heterodera schachtii, Heterodera trifolii, and other Heterodera species; Seed gall nematodes, Anguina species; Stem and foliar nematodes, Aphelenchoides species; Sting nematodes, Belonolaimus longicaudatus and other Belonolaimus species; Pine Belonolaimus longicaudatus and other Belonolaimus species; Pine nematodes, Bursaphelenchus xylophilus and other Bursaphelenchus species; Ring nematodes, Criconema species, Criconemella species, Criconemoides species, Mesocriconema species; Stem and bulb nematodes, Ditylenchus destructor, Ditylenchus dipsaci and other Ditylenchus species; Awl nematodes, Dolichodorus species; Spiral nematodes, Heliocotylenchus multicinctus and other Helicotylenchus species; Sheath and sheathoid nematodes, Hemicycliophora species and Hemicriconemoides species; Hirshmanniella species; Lance nematodes, Hoploaimus species; false rootknot nematodes, Nacobbus species; Needle nematodes, Longidorus elongatus and other Longidorus species; Lesion nematodes, Pratylenchus neglectus, Pratylenchus penetrans, Pratylenchus curvitatus, Pratylenchus goodeyi and other Pratylenchus species; Burrowing nematodes, Radopholus similis and other Radopholus species; Reniform nematodes, Rotylenchus robustus and other Rotylenchus species; Scutellonema species; Stubby root nematodes, Trichodorus primitivus and other Trichodorus species, Paratrichodorus species; Stunt nematodes, Tylenchorhynchus claytoni, Tylenchorhynchus dubius and other Tylenchorhynchus species; Citrus nematodes, Tylenchulus species; Dagger nematodes, Xiphinema species; and other plant parasitic nematode species.

The compounds of the formula I and their salts are also useful for controlling arachnids (Arachnoidea), such as acarians (Acarina), e.g. of the families Argasidae, Ixodidae and Sarcoptidae, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei, and Eriophyidae spp. such as Aculus schlechtendali, Phyllocoptrata oleivora and Eriophyes sheldoni; Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetranychus pacificus, Tetranychus telarius and Tetranychus urticae, Panonychus ulmi, Panonychus citri, and oligonychus pratensis.

Compounds of the formula I are particularly useful for controlling insects, preferably sucking or piercing insects such as insects from the genera Thysanoptera, Hymenoptera, Orthoptera and Homptera, in particular the following species:

Thysanoptera (thrips): Frankliniella fusca, Frankliniella occidentalis, Frankliniella tritici, Scirtothrips citri, Thrips oryzae, Thrips palmi and Thrips tabaci, Hymenoptera: Athalia rosae, Atta cephalotes, Atta sexdens, Atta texana, Hoplocampa minuta, Hoplocampa testudinea, Monomorium pharaonis, Solenopsis geminata and Solenopsis invicta, Orthoptera: Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus;

Homoptera, in particular aphids: Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Drey-

*fusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii;*

In the methods according to the invention the pests are controlled by contacting the target parasite/pest, its food supply, habitat, breeding ground or its locus with a pesticidally effective amount of compounds of formula I or with a salt thereof or with a composition, containing a pesticidally effective amount of a compound of formula I or a salt thereof.

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

The aforementioned compositions are particularly useful for protecting crop plants against infestation of said pests or for combating these pests in infested plants.

For use in treating crop plants, the rate of application of the active ingredients of this invention may be in the range of 0.1 g to 4000 g per hectare, desirably from 25 g to 600 g per hectare, more desirably from 50 g to 500 g per hectare.

In accordance with one variant of the present invention, a further subject of the invention is a method of treating soil by the application, in particular into the seed drill, e.g. in form of a granular formulation containing compounds of formula I alone or in mixture with other active ingredients. This method is advantageously employed in seedbeds of cereal, maize, cotton and sunflower. For cereals and maize, the rates of application may depend from the active ingredients used, and may range between 50 and 500 per hectare for one active ingredient and between 50 and 200 g per hectare for the other active ingredient.

In the case of soil treatment or of application to the pests dwelling place or nest, the quantity of active ingredient ranges from 0.0001 to 500 g per 100 $m^2$, preferably from 0.001 to 20 g per 100 $m^2$.

The compounds of the invention may also be applied against non-crop insect pests, such as ants, termites, wasps, flies, mosquitos, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

In the method of this invention compounds I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphates: acephate, azamethiphos, azinphos-ethyl, azinphosmethyl, chlorethoxyfos, chlorfenvinphos, chlormephos, chlorpyrifos, chlorpyrifosmethyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-, yfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, prallethrin, resmethrin, RU 15525, silafluofen, tefluthrin, tetramethrin, tralomethrin, transfluthrin, ZXI 8901;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), thiacloprid, thiocyclam, thiosultap-sodium and AKD1022.

M.6. GABA gated chloride channel antagonist compounds: chlordane, endosulfan, gamma-HCH (lindane); acetoprole, ethiprole, fipronil, pyrafluprole, pyriprole, vaniliprole, the phenylpyrazole compound of formula $M^{6.1}$ ($M^{6.1}$)

M.7. Chloride channel activators: abamectin, emamectin benzoate, milbemectin, lepimectin;

M.8. METII compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. octapaminergic agonsits: amitraz;

M.21. ryanodine receptor modulators: flubendiamide;

M.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, tartar emetic;

M.23. N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl;

M.24. Anthranilamides: chloranthraniliprole, the compound of formula $M^{24.1}$ ($M^{24.1}$)

A.25. Malononitrile compounds: $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, $CF_3CF_2CH_2C(CN)_2CH_2(CF_2)_3CF_2H$, 2-(2,2,3,3,4,4,5,5-octafluoropentyl)-2-(3,3,4,4,4-pentafluorobutyl)-malonodinitrile, and $CF_2HCF_2CF_2CF_2CH_2C(CN)_2CH_2CH_2CF_2CF_3$;

A.26. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

The commercially available compounds of the group A may be found in The Pesticide Manual, 13$^{th}$ Edition, British Crop Protection Council (2003) among other publications.

Thioamides of formula $M^{6.1}$ and their preparation have been described in WO 98/28279. Lepimectin is known from Agro Project, PJB Publications Ltd, November 2004. Benclothiaz and its preparation have been described in EP-A1454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chloranthraniliprole has been described in WO 01/70671, WO 03/015519 and WO 05/118552. Anthranilamide derivatives of formula $M^{24.1}$ have been described in WO 01/70671, WO 04/067528 and WO 05/118552. Cyflumetofen and its preparation have been described in WO 04/080180. The aminoquinazolinone compound pyrifluquinazon has been described in EP A 109 7932. The malononitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, $CF_3CF_2CH_2C(CN)_2CH_2(CF_2)_3CF_2H$, 2-(2,2,3,3,4,4,5,5-octafluoropentyl)-2-(3,3,4,4,4-pentafluorobutyl)-malonodinitrile, and $CF_2HCF_2CF_2CF_2CH_2C(CN)_2CH_2CH_2CF_2CF_3$ have been described in WO 05/63694.

Formulations

For use in a method according to the present invention, the compounds I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-methyl-pyrrolidone (NMP),N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen und benzyl alcohol hemiformal Suitable thickeners are compounds, which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol® 23 (Rhone Poulenc) or Veegum® (from R. T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:
1. Products for dilution with water. For seed treatment purposes, such products may be applied to the seed diluted or undiluted.

A) Water-soluble Concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-dispersible Granules and Water-soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-dispersible Powders and Water-soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 parts by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

Animal Health

Activity of compounds against agricultural pests does not suggest their suitability for control of endo- and ectoparasites in and on animals which requires, for example, low, nonemetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (*Siphonaptera*), e.g. *Ctenocephalides felis, Ctenocephalides canis, Xenopsylla cheopis, Pulex irritans, Tunga penetrans,* and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) und Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Pso-*

*roptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I, and compositions containing them are particularly useful for the control of pests from the orders Diptera, Siphonaptera and Ixodida.

Moreover, the use of the compounds of formula I, and compositions containing them for combating mosquitoes is especially preferred.

The use of the compounds of formula I, and compositions containing them for combating flies is a further preferred embodiment of the present invention.

Furthermore, the use of the compounds of formula I, and compositions containing them for combating fleas is especially preferred.

The use of the compounds of formula I, and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils, which are suitable for injection.

Suitable solubilizers are solvents, which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methyl-ethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions, which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methyl-pyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether;
ampholytic surfactants such as di-sodium N-lauryl-p-iminodipropionate or lecithin;
anionic surfactants, such as sodium lauryl sulfate, fatty alcohol ether sulfates, mono/dialkyl polyglycol ether orthophosphoric acid ester monoethanolamine salt;
cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries, which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants, which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions, which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations, which are diluted before use, contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

In the treatment of seeds the corresponding formulations are applied by treating the seeds with an effective amount of the active compound. Herein, the application rates of the active compound are generally from 0.1 g to 10 kg per 100 kg of seed, preferably from 1 g to 5 kg per 100 kg of seed, in particular from 1 g to 2.5 kg per 100 kg of seed. For specific crops such as lettuce the rate can be higher.

Compositions, which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Preferred FS formulations of compounds of formula I for seed treatment usually comprise from 0.1 to 80% by weight (1 to 800 g/L) of the active ingredient, from 0.1 to 20% by weight (1 to 200 g/L) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a Gelling Agent is Carrageen (Satiagel®)

In the treatment of seed, the application rates of the compounds I are generally from 0.1 g to 10 kg per 100 kg of seed, preferably from 1 g to 5 kg per 100 kg of seed, in particular from 1 g to 1000 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed.

The present invention is now illustrated in further details by the following examples.

Some of the preferred compound examples of formula I* for use in the methods according to the present invention are characterized by their melting point in the following table C:

TABLE C

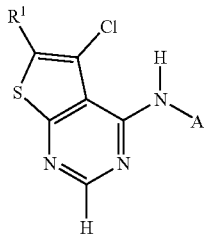

(formula I*)

| Compound n° | R¹ | A1 R⁴ | A1 R⁵ | A1 R⁶ | A2 R⁷ | A2 R⁸ | A2 R⁹ | A3 R¹⁰ | Physical data: $T_{mp}$ (melting point) in [° C.] |
|---|---|---|---|---|---|---|---|---|---|
| C.1 | H | | | | H | $CH_3$ | $OCF_2CHF_2$ | | 84-87 |
| C.2 | H | | | | H | $CH_3$ | $OCF_3$ | | 79-80 |
| C.3 | H | | | | H | $CH_3$ | $OCHF_2$ | | 102-103 |
| C.4 | H | | | | H | $C_2H_5$ | $OCF_2CHFCF_3$ | | oil |
| C.5 | H | H | H | $OCF_3$ | | | | | 77-79 |
| C.6 | H | | | | | | | cis-$C(CH_3)_3$ | 107-109 |
| C.7 | H | | | | | | | cis-$CH(CH_3)C_2H_5$ | 70-73 |
| C.8 | H | | | | | | | trans-$CF_3$ | resin |
| C.9 | H | | | | | | | trans-$CH_2CH_2CF_3$ | resin |
| C.10 | H | | | | | | | cis-$CF_3$ | 105-109 |
| C.11 | H | | | | | | | $CH_2CH_2CF_3$ | resin |
| C.12 | CHO | | | | | | | cis-$C(CH_3)_3$ | 90-91 |
| C.13 | $CHCl_2$ | | | | | | | cis-$O(CH_3)_3$ | 178-185 |
| C.14 | $CH_3$ | | | | | | | cis-$O(CH_3)_3$ | 128-133 |
| C.15 | $CH_3$ | | | | H | $CH_3$ | $OCF_2CHF_2$ | | resin |
| C.16 | $CH_3$ | | | | H | $CH_3$ | OCF3 | | 68-72 |
| C.17 | $CH_3$ | | | | H | $CH_3$ | $OCHF_2$ | | 77-81 |
| C.18 | $CH_3$ | | | | | | | cis-$CH(CH_3)C_2H_5$ | oil |
| C.19 | $CH_3$ | H | H | $OCF_3$ | | | | | 73-77 |
| C.20 | $CH_3$ | | | | | | | trans$CH_2CH_2CF_3$ | 130-135 |
| C.21 | $CH(OCH_3)_2$ | | | | | | | cis-$O(CH_3)_3$ | oil |
| C.22 | $CHCH_2$ | | | | | | | cis-$O(CH_3)_3$ | 114-127 |
| C.23 | CH=N—OH | | | | | | | cis-$O(CH_3)_3$ | 214-215 |
| C.24 | CH=N—$OCH_3$ | | | | | | | cis-$O(CH_3)_3$ | resin (E-isomer) |
| C.25 | CH=N—$OCH_3$ | | | | | | | cis-$O(CH_3)_3$ | 90-93 (E/Z-isomer 2:1) |
| C.26 | CN | | | | | | | cis-$O(CH_3)_3$ | 160-166 |
| C.27 | CH=N—$OC_2H_5$ | | | | | | | cis-$C(CH_3)_3$ | 146-157 (E-isomer) |
| C.28 | CH=N—$OC_2H_5$ | | | | | | | cis-$C(CH_3)_3$ | resin (E/Z-isomer 2:1) |
| C.29 | $C_2H_5$ | | | | | | | cis-$C(CH_3)_3$ | 70-75 |
| C.30 | $C_2H_5$ | | | | H | $CH_3$ | $OCF_2CHF_2$ | | oil |
| C.31 | $C_2H_5$ | | | | H | $CH_3$ | OCF3 | | oil |
| C.32 | $C_2H_5$ | | | | H | $CH_3$ | $OCHF_2$ | | oil |
| C.33 | $C_2H_5$ | | | | | | | cis-$CH(CH_3)C_2H_5$ | oil |

SYNTHESIS EXAMPLES

S.1 (5-Chloro-thieno[2,3-d]pyrimidin-4-yl)-[1-(4-trifluoromethoxy-phenyl)-ethyl]-amine Compound Example C.2

0.5 g (2.4 mmol) 4,5-dichloro-thieno-[2,3-d]-yprimidine are solved in 25 ml toluol. Subsequently 0.29 g (2.7 mmol) triethylamin, a catalytic amount of tetrabutylammoniumiodide and 0.5 g (2.5 mmol) (S)-1-(4-trifluoromethoxyphenyl)-ethylamin are added. The solution is heated under for reflux for 4 hours, and stirred further 12 hours at room temperature. The solvent is destillated, the residue is reverted in $CH_2Cl_2$ and is washed with 2N HCl and $H_2O$. The residue is cleaned up by flash chromatography after being dryed and concentrated. The yield of compound C.3 obtained is 0.5 g (1.4 mmol, 56% of the theoretical yield) and has a melting point Tmp of 79-80° C.

$^1$H-NMR ($CDCl_3$): 8.45 (s, 1H), 7.45 (d, 2H), 7.20 (d, 2H), 7.10 (s, 1H), 6.80 (d, 1H), 5.55 (t, 1H), 1.65 (d, 3H);

S.2 cis-(4-tert-Butyl-cyclohexyl)-(5-chloro-thieno[2,3-d]pyrimidin-4-yl)-amine

Compound Example C.6

2 g (9.7 mmol) 4,5-dichloro-thieno-[2,3-d]-yprimidine are solved in 25 ml toluol. Subsequently 1.1 g (10.7 mmol) triethylamin, a catalytic amount of tetrabutylammoniumiodide and 1.6 g (10.2 mmol) cis-4-t-butylcyclohexylamine are added. The solution is heated under reflux for 8 hours, and stirred for further 12 hours at room temperature. The solvent is destillated, the residue is reverted in $CH_2Cl_2$ and is washed with 2N HCl and $H_2O$. The residue is cleaned up by flash chromatography after being dried and concentrated. The yield of compound C.6 obtained is 2.2 g (6.8 mmol, 70% of theoretical yield) and has a melting point $T_{mp}$ of 107-109° C.

$^1$H-NMR (CDCl$_3$): 8.45 (s, 1H), 7.10 (s, 1H), 6.90 (m, 1H), 4.55 (m, 1H), 2.05 (d, 2H), 1.75 (m, 2H), 1.60 (m, 2H), 1.30-1.10 (m, 3H), 0.90 (s, 9H)

S.3. (5-Chloro-thieno[2,3-d]pyrimidin-4-yl)-[2-(4-trifluoromethoxy-phenyl)-ethyl]-amine Compound Example C.5

0.5 g (2.4 mmol) 4,5-dichloro-thieno-[2,3-d]-yprimidine are solved in 20 ml toluol. Subsequently 0.271 g (2.7 mmol) triethylamin, a catalytic amount of tetrabutylammoniumiodide and 0.55 g (2.7 mmol) 2-(4-trifluoromethoxyphenyl)-ethylamin are added. The solution is heated under reflux for 6 hours, and stirred further 12 hours at room temperature. The solvent is destillated, the residue is reverted in $CH_2Cl_2$ and is washed with 2N HCl and $H_2O$. The residue is stirred and sucked off with hexane after being dried and concentrated. The yield of compound C.5 obtained is 0.73 g (1.9 mmol, 76% of theoretical yield) and has a melting point $T_{mp}$ of 77-79° C.

$^1$H-NMR (CDCl$_3$): 8.50 (s, 1H), 7.25 (d, 2H), 7.15 (d, 2H), 7.05 (s, 1H), 6.55 (bs, 1H), 3.90 (t, 2H), 3.00 (t, 2H);

Biological Examples of Action Against Pests

In the following tests, if not precised otherwise, the formulated solutions of some of the compound examples were diluted to an active ingredient concentration of 300 ppm, and the diluted solutions were applied in the below mentioned tests.

B.1. Cotton Aphid (*aphis gossypii*), Mixed Life Stages

The active compounds were formulated in 50:50 acteone/water and 100 ppm Kinetic™ surfactant Cotton plants at the cotyledon stage were infested prior to treatment by placing a heavily infested leaf from the main aphid colony on top of each cotyledon. The aphids were allowed to transfer overnight and the host leaf was removed. The infested cotyledons were then dipped and agitated in the test solution for 3 seconds and allowed to dry in a fume hood. Test plants were maintained under fluorescent lighting in a 24-hr photoperiod at 25° C. and 20-40% relative humidity. Aphid mortality on the treated plants, relative to mortality on untreated check plants, was determined after 5 days.

In this test compound examples 1-7, 9, 10, 11 and 16-19 provided at 100 ppm at least 90% mortality of cotton aphid (*Aphis gossypii*, mixed life stages) in comparison with untreated controls.

B.2. Green Peach Aphid (*Myzus persicae*), Mixed Life Stages

Bell pepper plants at the first true-leaf stage were infested prior to treatment by placing heavily infested leaves from the main aphid colony on top of the treatment plants. The aphids were allowed to transfer overnight to accomplish an infestation of 30-40 aphids per plant and the host leaves were removed. The infested leaves of the test plants were then dipped and agitated in the test solution for 3 seconds and allowed to dry in a fume hood. Test plants were maintained under fluorescent lighting in a 24-hr photoperiod at 25° C. and 20-40% relative humidity. Aphid mortality on the treated plants, relative to mortality on untreated check plants, was determined after 5 days.

In this test compound examples 1-7, 9-11, 16-18, 30, 31 and 33 provided at 100 ppm at least 90% mortality of green peach aphid in comparison with untreated controls.

B3. Rice Plant Hopper (*Nilaparvata lugens*)

Rice seedlings were cleaned and washed 24 hours before spraying. The active compounds were formulated in 50:50 acetone:water and 0.1% vol/vol surfactant (EL 620) was added. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, compounds 1, 2, 5, 6, 7 and 9-11 at 100 ppm showed at least 90% mortality.

B.4. Southern Armyworm (*spodoptera eridania*), $2^{nd}$-$3^{rd}$ Instar Larvae

The active compounds were formulated as a 10.000 ppm solution in a mixture of 35% acetone and water, which was diluted with water, if needed.

Sieva lima bean foliage, expanded to the first true leaves, were dipped and agitated in the test solution for 3 seconds and then allowed to dry in a fume hood. The treated plant was then placed in 25-cm plastic perforated zip enclosure bags, ten $2^{nd}$-instar larvae were added, and the bags sealed. After 4 days, observations were made of mortality, plant feeding, and of any interference with larval growth.

In this test, compounds 1, 5, 7, 10, 11 and 15 at 100 ppm showed at least 60% mortality in comparison with untreated controls.

B.5. Silverleaf Whitefly (*Bemisia argentifolii*)

The active compounds were formulated in 50:50 acetone:water and 100 ppm Kinetic™ surfactant.

Selected cotton plants were grown to the cotyledon state (one plant per pot). The cotyledons were dipped into the test solution to provide complete coverage of the foliage and placed in a well-vented area to dry. Each pot with treated seedling was placed in a plastic cup and 10 to 12 whitefly adults (approximately 3-5 day old) were introduced. The insects were colleted using an aspirator and an 0.6 cm, non-toxic TygonO tubing (R-3603) connected to a barrier pipette tip. The tip, containing the collected insects, was then gently inserted into the soil containing the treated plant, allowing insects to crawl out of the tip to reach the foliage for feeding. The cups were covered with a reusable screened lid (150 micron mesh polyester screen PeCap from Tetko Inc). Test plants were maintained in the holding room at about 25° C. and 20-40% relative humidity for 3 days avoiding direct exposure to the fluorescent light (24 hour photoperiod) to prevent trapping of heat inside the cup. Mortality was assessed 3 days after treatment of the plants.

In this test, compounds 1-7, 11, 15, 16 and 18 at 100 ppm showed at least 90% mortality compared to untreated controls.

B.6. Colorado Potato Beetle (*Leptinotarsa decemlineata*)

Potato plants were utilized for bioassays. Excised plant leaves were dipped into 1:1 acetone/water dilutions of the active compounds. After the leaves had dried, they were individually placed onto water-moistened filter paper on the bottoms of Petri dishes.

Each dish was infested with 5-7 larvae and covered with a lid. Each treatment dilution was replicated 4 times. Test dishes were held at approximately 27° C. and 60% humidity.

Numbers of live and morbid larvae were assessed in each dish at 5 days after treatment application, and mortality percentage was calculated.

In this test, compounds 1-7,9,13-16, 18-21 and 25 at 100 ppm showed at least 90% mortality compared to untreated controls.

B.7 Rice Green Leafhopper (*Nephotettix virescens*)

Rice seedlings were cleaned and washed 24 hours before spraying. The active compounds were formulated in 50:50 acetone:water, and 0.1% vol/vol surfactant (EL 620) was added. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, compounds 2, 7, 5, 6, 10 and 11 at 100 ppm showed at least 60% mortality.

B.8 Bean Aphid (*aphis fabae*)

The active compounds were formulated in 50:50 acetone:water and 100 ppm Kinetic™ surfactant.

Nasturtium plants grown in Metro mix in the 1st leaf-pair stage (variety 'Mixed Jewle') were infested with approximately 2-30 laboratory-reared aphids by placing infested cut plants on top of the test plants. The cut plants were removed after 24 hr. Each plant was dipped into the test solution to provide complete coverage of the foliage, stem, protruding seed surface and surrounding cube surface and allowed to dry in the fume hood. The treated plants were kept at about 25° C. with continuous fluorescent light. Aphid mortality was determined after 3 days.

In this test, compounds 1-3, 6 and 7 at 100 ppm showed at least 60% mortality.

B.9 Cowpea Aphid (*aphis craccivora*)

The active compounds were formulated in 50:50 acetone:water. Potted cowpea plants colonized with 100-150 aphids of various stages were sprayed after the pest population has been recorded. Population reduction was recorded after 24, 72, and 120 hours.

In this test, compounds 1-7, 9-11, 14-16, 18, 20, 25, 29 and 30 at 100 ppm showed at least 75% mortality.

Comparative Test:

Compounds of the present invention showed further an unexpected higher biological activity in comparison to those disclosed in EP-A 0447891. The biological activity in tables B.1 and B.2 was evaluated on scale range from 0% as showing no biological activity to 100% as having total control. The comparative biological tests were conducted as described above.

TABLE B.1

| Organism | Concentration (ppm) | compound example C.6 $R^{10} = -C(CH_3)_3$ | (example 288 in EP-A 0447891) $R^{10} = H$ |
|---|---|---|---|
| *Nilaparvata lugens* | 300 | 100 | 0 |
| *Aphis gossypii* | 300 | 100 | 75 |
| *Myzus persicae* | 300 | 100 | 50 |
| *Spodoptera eridania* | 300 | 100 | 0 |
| *Bemesia argentifolia* | 300 | 100 | 0 |

TABLE B.2

| Organism | Concentration (ppm) | compound example C.2 $R^9: -OCF_3$ | (example 378 in EP-A-0447891) $R^9: H$ |
|---|---|---|---|
| *Nilaparvata lugens* | 300 | 100 | 0 |
| *Aphis gossypii* | 300 | 100 | 100 |
| *Myzus persicae* | 300 | 100 | 100 |
| *Bemesia argentifolia* | 300 | 100 | 0 |

We claim:
1. A method for combating or controlling insects, arachnids or nematodes comprising contacting an insect, arachnid or nematode or their food supply, habitat or breeding grounds with a pesticidally effective amount of a 4-Amino-5-chloro-thieno[2,3-d]-pyrimidine compound of formula I or a composition comprising a compound of formula I:

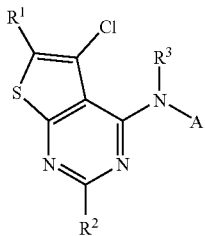

formula I wherein
R$^1$ is selected from the group consisting of hydrogen, halogen, formyl, $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino, di($C_1$-$C_{10}$-alkyl)amino, CN, CHNOH, CHNOCH$_3$ and CHNOC$_2$H$_5$;

R$^2$ is selected from the group consisting of hydrogen, halogen, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino and di($C_1$-$C_{10}$-alkyl)amino;

R$^3$ is hydrogen or $C_1$-$C_{10}$-alkyl; and
A is

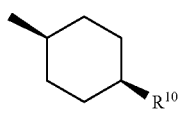
(A3)

wherein
R$^{10}$ is $C_3$-$C_{10}$-alkyl or $C_1$-$C_{10}$-haloalkyl;
or an agriculturally acceptable salt thereof.

2. A method for protecting crops and growing plants from attack or infestation by insects, arachnids or nematodes comprising contacting a plant, or soil or water in which the plant is growing, with a pesticidally effective amount of an Amino-5-chloro-thieno[2,3-d]-pyrimidine compound of formula I or a composition comprising a compound of formula I:

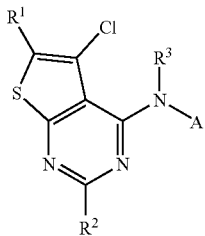

formula I wherein
R$^1$ is selected from the group consisting of hydrogen, halogen, formyl, $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino, di($C_1$-$C_{10}$-alkyl)amino, CN, CHNOH, CHNOCH$_3$ and CHNOC$_2$H$_5$;

R$^2$ is selected from the group consisting of hydrogen, halogen, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino and di($C_1$-$C_{10}$-alkyl)amino;

R$^3$ is hydrogen or $C_1$-$C_{10}$-alkyl; and
A is

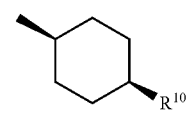
(A3)

wherein
R$_{10}$ is $C_3$-$C_{10}$-alkyl or $C_1$-$C_{10}$-haloalkyl;
or an agriculturally acceptable salt thereof.

3. A method for protecting seeds from soil insects and seedlings' roots and shoots from soil and foliar insects comprising contacting the seeds before sowing and/or after pregermination with a 4-Amino-5-chloro-thieno[2,3-d]-pyrimidine compound of formula I or a composition comprising a compound of formula I:

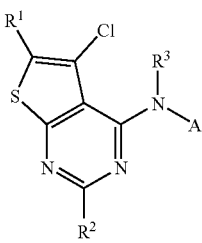

formula I wherein
R$^1$ is selected from the group consisting of hydrogen, halogen, formyl, $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino, di($C_1$-$C_{10}$-alkyl)amino, CN, CHNOH, CHNOCH$_3$ and CHNOC$_2$H$_5$;

R$^2$ is selected from the group consisting of hydrogen, halogen, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino and di($C_1$-$C_{10}$-alkyl)amino;

R$^3$ is hydrogen or $C_1$-$C_{10}$-alkyl; and

A is

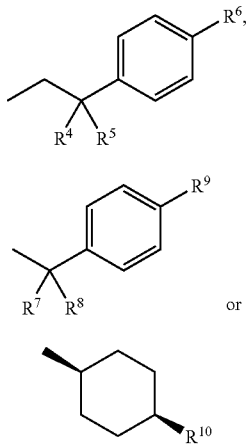

(A1)

(A2)

(A3)

wherein
R$^{10}$ is C$_3$-C$_{10}$-alkyl or C$_1$-C$_{10}$-haloalkyl;
or an agriculturally acceptable salt thereof.

4. A method for treating, controlling, preventing or protecting animals against infestation or infection by fleas, flies, mosquitoes, lice, ticks, mites and nematodes by administering to the animals a parasitically effective amount of a 4-Amino-5-chloro-thieno[2,3-d]-pyrimidine compound of formula I or a composition comprising a compound of formula I:

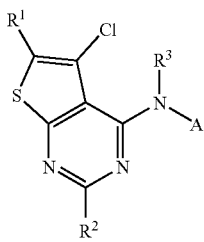

formula I wherein
R$^1$ is selected from the group consisting of hydrogen, halogen, formyl, C$_1$-C$_{10}$-alkyl, C$_2$-C$_{10}$-alkenyl, C$_2$-C$_{10}$-alkynyl, C$_1$-C$_{10}$-haloalkyl, C$_2$-C$_{10}$-haloalkenyl, C$_2$-C$_{10}$-haloalkynyl, C$_1$-C$_{10}$-alkoxy, C$_1$-C$_6$-alkoxy-C$_1$-C$_6$-alkyl, C$_1$-C$_{10}$-haloalkoxy, C$_1$-C$_{10}$-alkylthio, C$_1$-C$_{10}$-alkylsulfinyl, C$_1$-C$_{10}$-alkylsulfonyl, C$_1$-C$_{10}$-alkylamino, di(C$_1$-C$_{10}$-alkyl)amino, CN, CHNOH, CHNOCH$_3$ and CHNOC$_2$H$_5$;
R$^2$ is selected from the group consisting of hydrogen, halogen, C$_1$-C$_{10}$alkyl, C$_1$-C$_{10}$-haloalkyl, C$_1$-C$_{10}$-alkoxy, C$_1$-C$_6$-alkoxy-C$_1$-C$_6$-alkyl, C$_1$-C$_{10}$-haloalkoxy, C$_1$-C$_{10}$-alkylthio, C$_1$-C$_{10}$-alkylsulfinyl, C$_1$-C$_{10}$-alkylsulfonyl, C$_1$-C$_{10}$-alkylamino and di(C$_1$-C$_{10}$-alkyl)amino;
R$^3$ is hydrogen or C$_1$-C$_{10}$-alkyl; and A is

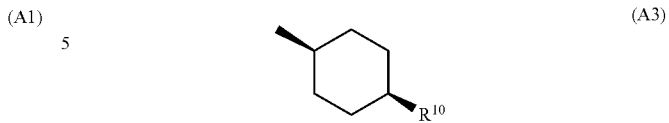

(A3)

wherein
R$^{10}$ is C$_3$-C$_{10}$-alkyl or C$_1$-C$_{10}$-haloalkyl;
or a veterinary acceptable salt thereof.

5. The method of claim 4, wherein R$^1$ and R$^2$ are selected, independently from one another, from the group consisting of hydrogen and C$_1$-C$_6$-alkyl.

6. The method of claim 4, wherein R$^{10}$ is a branched C$_3$-C$_{10}$-alkyl.

7. The method of claim 4, wherein R$^{10}$ is iso-propyl, sec-butyl or tert-butyl.

8. The method of claim 4, wherein the compound is cis-(4-tert-Butyl-cyclohexyl)(5-chloro-thieno[2,3-d]pyrimidin-4-yl)-amine.

9. A 4-Amino-5-chloro-thieno[2,3-d]-pyrimidine compound of formula I-A3:

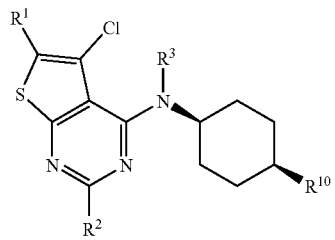

formula I-A3 wherein
R$^1$ is selected from the group consisting of hydrogen, halogen, formyl, C$_1$-C$_{10}$-alkyl, C$_2$-C$_{10}$-alkenyl, C$_2$-C$_{10}$-alkynyl, C$_1$-C$_{10}$-haloalkyl, C$_2$-C$_{10}$-haloalkenyl, C$_2$-C$_{10}$-haloalkynyl, C$_1$-C$_{10}$-alkoxy, C$_1$-C$_6$-alkoxy-C$_1$-C$_6$-alkyl, C$_1$-C$_{10}$-haloalkoxy, C$_1$-C$_{10}$-alkylthio, C$_1$-C$_{10}$-alkylsulfinyl, C$_1$-C$_{10}$-alkylsulfonyl, C$_1$-C$_{10}$-alkylamino, di(C$_1$-C$_{10}$-alkyl)amino, CN, CHNOH, CHNOCH$_3$ and CHNOC$_2$H$_5$;
R$^2$ is selected from the group consisting of hydrogen, halogen, C$_1$-C$_{10}$alkyl, C$_1$-C$_{10}$-haloalkyl, C$_1$-C$_{10}$-alkoxy, C$_1$-C$_6$-alkoxy-C$_1$-C$_6$-alkyl, C$_1$-C$_{10}$-haloalkoxy, C$_1$-C$_{10}$-alkylthio, C$_1$-C$_{10}$-alkylsulfinyl, C$_1$-C$_{10}$-alkylsulfonyl, C$_1$-C$_{10}$-alkylamino, and di(C$_1$-C$_{10}$-alkyl)amino;
R$^3$ is hydrogen or C$_1$-C$_{10}$-alkyl; and
R$^{10}$ is C$_3$-C$_{10}$-alkyl or C$_1$-C$_{10}$-haloalkyl;
or an agriculturally or veterinary acceptable salt thereof.

10. The compound of claim 9, wherein
R$^1$, R$^2$ are independently from one another, from the group consisting of hydrogen and C$_1$-C$_6$-alkyl.

11. The compound of claim 9, wherein R$^{10}$ is a branched C$_3$-C$_{10}$-alkyl.

12. The compound of claim 9, wherein R$^{10}$ is iso-propyl, sec-butyl or tert-butyl.

13. The compound of claim 9, wherein the compound is cis-(4-tert-Butyl-cyclohexyl)-(5-chloro-thieno[2,3-d]pyrimidin-4-yl)-amine.

14. An agricultural or veterinary composition comprising the compound of claim 9 or an enantiomer, diastereomer or salt thereof and an inert liquid and/or solid carrier.

15. The method of claim 4 comprising orally, topically or parenterally administering or applying to the animals a parasitically effective amount of the compound of formula I or a veterinary acceptable salt thereof.

16. The method of claim 3, wherein the compound is applied in an amount of from 100 mg to 10 kg per 100 kg of seeds.

17. The method of claim 3, wherein the resulting plant's roots and shoots are protected.

18. A seed comprising the compound of claim 9 or an agriculturally useful salt thereof, in an amount of from 0.1 g to 10 kg per 100 kg of seed.

* * * * *